United States Patent [19]

Wehner et al.

[11] 4,327,016
[45] Apr. 27, 1982

[54] ORGANOTIN COMPOUNDS, AND THEIR USE

[75] Inventors: Wolfgang Wehner, Zwingenberg; Horst Müller, Fürth; Hans-Günter Köstler, Heppenheim, all of Fed. Rep. of Germany

[73] Assignee: Ciba-Geigy Corporation, Ardsley, N.Y.

[21] Appl. No.: 145,417

[22] Filed: May 1, 1980

[30] Foreign Application Priority Data

May 7, 1979 [CH] Switzerland .................. 4255/79

[51] Int. Cl.³ .................. C07F 7/22; C08K 5/58
[52] U.S. Cl. .................. 524/180; 260/429.7; 524/567
[58] Field of Search .................. 260/429.7, 45.75 S

[56] References Cited

U.S. PATENT DOCUMENTS

| | | | |
|---|---|---|---|
| 3,417,116 | 12/1968 | Considine et al. | 260/429.7 |
| 3,440,255 | 4/1969 | Matsuda et al. | 260/429.7 |
| 3,471,538 | 10/1969 | Considine et al. | 260/429.7 |
| 4,080,363 | 3/1978 | Hutton et al. | 260/45.75 S |
| 4,122,064 | 10/1978 | Scheidl et al. | 260/429.7 |
| 4,134,878 | 1/1979 | Burley et al. | 260/45.75 S |
| 4,158,669 | 6/1979 | Wirth et al. | 260/429.7 |
| 4,195,029 | 3/1980 | Otto et al. | 260/429.7 |
| 4,196,137 | 4/1980 | Wirth et al. | 260/429.7 |
| 4,210,595 | 7/1980 | Wirth et al. | 260/429.7 |

Primary Examiner—Helen M. S. Sneed
Attorney, Agent, or Firm—Harry Falber

[57] ABSTRACT

Compounds of the formula

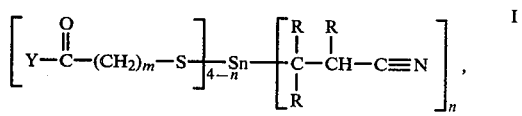

wherein each R independently is hydrogen or $C_1$–$C_4$ alkyl, Y is the —OR' or —S—R" group, in which R' is $C_{12}$–$C_{16}$ alkyl and R" is $C_8$–$C_{20}$ alkyl, $C_2$–$C_{20}$ alkenyl, $C_6$–$C_{20}$ alkyl or $C_7$–$C_{20}$ aralkyl, m is an integer from 1 to 6, and n is 1 or 2. These compounds are stabilizers for halogen-containing thermoplastics.

10 Claims, No Drawings

ORGANOTIN COMPOUNDS, AND THEIR USE

The present invention relates to cyano-substituted mono- and diorganotin compounds, their use as heat stabilisers, new intermediates for the manufacture of cyano-substituted mono- and diorganotin compounds, and a process for obtaining these intermediates.

Substantial economic importance attaches to organotin compounds as stabilisers for halogen-containing thermoplastics. For example, German Offenlegungsschrift No. 2 822 508 teaches that a mixture consisting of an organotin stabiliser, such as an unsubstituted or cyano-substituted organotin mercaptide, and an alkali or alkaline earth metal mercaptide, is an especially effective heat stabiliser for PVC.

It is also known from U.S. Pat. No. 3,471,538 to use the compound of the formula $(CN-CH_2CH_2)_2$-$Sn(-S-CH_2-COO-i-C_8H_{17})_2$ as a heat stabiliser for polymers.

Although the known organotin compounds are effective stabilisers, they have the disadvantage that they are very expensive. The need therefore exists for new stabilisers which can be obtained by economic methods using easily obtainable starting materials.

It has now been found that cyano-substituted organotin compounds can be readily obtained from easily prepared intermediates and that, surprisingly, they impart good light and heat stability to chlorinated polymers.

Accordingly, the present invention provides compounds of the formula I

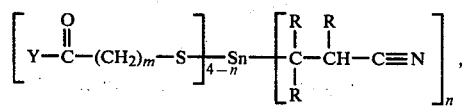

wherein each R independently is hydrogen or $C_1$–$C_4$ alkyl, Y is the —OR' or —R'' group, in which R' is $C_{12}$–$C_{16}$ alkyl and R'' is $C_8$–$C_{20}$ alkyl, $C_2$–$C_{20}$ alkenyl, $C_6$–$C_{20}$ aryl or $C_7$–$C_{20}$ aralkyl, m is an integer from 1 to 6, and n is 1 to 2.

R as $C_1$–$C_4$ alkyl is e.g. methyl, ethyl, isopropyl or n-butyl. It is preferred that R is hydrogen or methyl, with hydrogen being most preferred.

R' as $C_{12}$–$C_{16}$ alkyl is e.g. n-dodecyl, 2-methyldodecyl, 4-tetradecyl and n-hexadecyl. Preferably R' is n-tetradecyl or n-hexadecyl, with n-tetradecyl being most preferred.

R'' as $C_8$–$C_{20}$ alkyl is e.g. 2-ethylhexyl, n-decyl, n-dodecyl, n-tetradecyl, 16-methylheptadecyl, n-nonadecyl or 2-eicosyl. Preferably R'' is $C_8$–$C_{12}$ alkyl, most preferably n-dodecyl.

R'' as $C_8$–$C_{20}$ alkenyl is e.g. vinyl, allyl, 1-pentenyl, 3-penten-2-methyl-2-yl, 9-octadecen-1-yl, preferably vinyl and allyl, with vinyl being most preferred.

R'' can be an unsubstituted or a substituted aryl group containing a total of 6 to 20 carbon atoms. An unsubstituted aryl group is e.g. phenyl or naphthyl, especially phenyl. When the aryl group is substituted, possible substituents are one or two alkyl groups of 1 to 8 carbon atoms. Examples of substituted aryl groups are tolyl, xylyl, ethylphenyl, n-octylphenyl, with tolyl and xylyl being preferred. Tolyl is the most preferred identity.

R'' as $C_7$–$C_{20}$ aralkyl is e.g. benzyl, α-phenylethyl, β-phenylethyl, αα-dimethylbenzyl, with benzyl and α-phenylethyl being preferred. The most preferred identity is benzyl.

Y is preferably the —OR' group. n is 1 or 2, especially 1. m is an integer from 1 to 6, and is preferably 1 or 2. Most preferably, m is 1.

Accordingly, preferred compounds are those of the formula I wherein Y is the —OR' group, m is 1 or 2, R is hydrogen or methyl, and n is 1.

Preferred compounds of the formula I are:

| | |
|---|---|
| $(n\text{-}C_{14}H_{29}-OOC-CH_2CH_2-S-)_3Sn-CH_2CH_2-CN$ | 1. |
| $(n\text{-}C_{16}H_{33}-OOC-CH_2-S-)_3Sn-CH_2CH_2-CN$ | 2. |
| $(n\text{-}C_{14}H_{29}-OOC-CH_2-S-)_3Sn-CH_2-CH(CH_3)-CN$ | 3. |
| $(n\text{-}C_{14}H_{29}-OOC-CH_2-S-)_2Sn(-CH_2-CH_2-CN)_2$ | 4. |
| $(n\text{-}C_{14}H_{29}-OOC-CH_2-S-)_3Sn-CH_2CH_2-CN$ | 5. |

Compounds 1 and 5 are especially preferred.

The compounds of the formula I can be obtained by methods which are known per se, as by those described in German Offenlegungsschrift No. 2 531 308, e.g. from a tin halide complex of the formula II

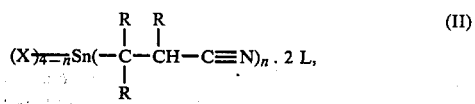

wherein X is chlorine, bromine or iodine, R and n have the given meanings, and L is a complexing solvent, and a mercaptan of the formula $HS-(CH_2)_mC(O)Y$, wherein m and Y have the given meanings.

The reaction of the tin compound with the mercaptan can be carried out both in stoichiometric amounts and with an excess of mercaptan. The reaction is conducted in an inert solvent, e.g. chloroform, advantageously in the presence of a weak base such as sodium bicarbonate, and at slightly elevated temperature, preferably in the temperature range from 20° to 50° C.

The complex compounds of the formula II are novel and likewise constitute an object of the invention. R in these compounds has the meaning assigned to it above and is especially hydrogen. X is chlorine, bromine or iodine, especially chlorine. L is a polar, complexing solvent. Suitable solvents are $C_1$–$C_4$ alkyl-substituted organic or inorganic acid amides, e.g. methyl formamide, dimethyl formamide, dimethyl acetamide, hexamethylphosphorus triamide, hexamethylphosphoric triamide, diethyl sulfamide. Preferably L is dimethyl formamide, dimethyl acetamide or hexamethylphosphoric triamide. The most preferred solvent is dimethyl formamide. n is 1 or 2, preferably 1.

The tin halides of the formula II are obtained by dehydration of the corresponding acid amides.

The dehydration of organic acid amides with phosphorus or sulfur compounds, e.g. thionyl chloride, according to the reaction scheme

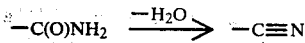

is known. The reaction is conducted preferably in a non-polar solvent, as described in Organic Synthesis, Collective Volume 4, page 436 (1867). Applied to organotin acid amides, this reaction is complicated by the coordinative forces which are active in the molecule:

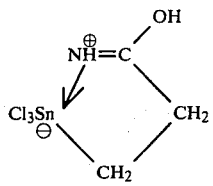

The formation of such a solvate-free mono-organotin compound in 3.4% yield in admixture with the corresponding di- or tri-compound is known from German Offenlegungsschrift No. 1 618 073.

It has now been found that, in the presence of strongly complexing solvents, the dehydration takes place under mild conditions in quantitative yield.

The invention therefore also relates to a process for the production of compounds of the formula II, which process comprises dehydrating a compound of the formula III

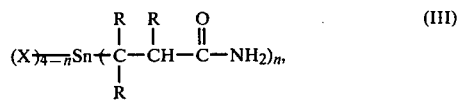

wherein X, R and n have the given meanings, in the presence of a dehydrating agent in a complexing solvent L.

L has the general and preferred meaning given hereinabove and is especially dimethyl formamide.

Suitable dehydrating agents are the compounds ordinarily employed, e.g. $SOCl_2$, $SO_2Cl_2$, $PCl_3$, $POCl_3$ or $PCl_5$. The preferred dehydrating agent is $SOCl_2$.

The reaction temperature is in the range from $-10°$ to $+10°$ C., with the preferred range being from $0°$ to $5°$ C.

The starting materials of the formula III are obtained in known manner, e.g. as described in Belgian Pat. No. 866 711.

The organotin compounds of the present invention are useful for stabilising chlorinated thermoplastics. To this end, they can be added to the chlorinated thermoplastics in the usual amounts. It is preferred to incorporate 0.01 to 10, especially 0.1 to 5 and most preferably 0.5 to 3% by weight of the organotin compounds, based on the chlorinated thermoplastics.

The preferred chlorinated thermoplastics are polymers or copolymers of vinyl chloride. Suspension and mass polymers, and emulsion polymers having a low content of emulsifier, are preferred. Examples of comonomers for the copolymers are: vinylidene chloride, trans-dichloroethane, ethylene, propylene, butylene, maleic acid, acrylic acid, fumaric acid and itaconic acid. Further suitable polymers are post-chlorinated polyolefins.

The stabilised thermoplastics are obtained by known methods by incorporating the stabilisers and, if desired, further stabilisers, in the polymer. A homogeneous mixture of stabiliser and polyvinyl chloride can be obtained e.g. using a two-roll mixer at 150° to 210° C. Depending on the end use of the moulding material, further additives can also be incorporated befor or simultaneously with the incorporation of the stabiliser. Examples of further additives are: lubricants, preferably monatan waxes or glycerol esters, plasticisers, fillers, modifiers such as impact strength additives, pigments, light stabilisers, UV absorbers, antioxidants or further costabilisers, for example phosphites or epoxidised fatty acid esters. The concurrent use of metal salts of barium, strontium, calcium, zinc, cadmium, lead, tin and magnesium with phenols or carboxylic acids (fatty acids, epoxidised fatty acids) is also possible. Mixtures of calcium and zinc carboxylates, in which the carboxylate group can contain from 8 to 20 carbon atoms, have proved to be especially advantageous.

The thermoplastics can be processed to mouldings by methods conventionally employed for the purpose, e.g. by extrusion, injection moulding or calendering.

Compared with known organotin compounds of the prior art, the compounds of this invention have better heat stabilising properties. The compounds are also of low volatility, which means that the loss of stabiliser during processing is particularly low. They can be obtained from the readily accessible intermediates of the formula II in simple manner, in high yield, and under very mild reaction conditions.

The intermediates of the formula II can also be obtained in simple manner, in high yield and under very mild reaction conditions. It is possible to obtain solvate-free compounds of the formula II, inter alia, during processing from the compounds of the formula I. It is especially advantageous that they are of low volatility, so that physiological irritations can be avoided during the processing to stabilisers. Because the compounds of the formula II are soluble only in polar solvents, the migration of plastic to the surrounding material during their formation in the stabilising process does not have to be reckoned with.

The invention is illustrated by the following Examples, in which parts are by weight.

EXAMPLE 1

(a) Manufacture of the intermediate

A three-necked flask equipped with stirrer, reflux cooler and bubble counter is charged with 15 g (0.05 mole) of β-carbaminoethyltin trichloride dissolved in 100 ml of dimethyl formamide (DMF). Then 7.2 g (0.06 mole) of $SOCl_2$ are slowly introduced at $0°$ C. such that the temperature does not rise above $+5°$ C. The reaction mixture is then allowed to stand for 3 hours at room temperature. Volatile constituents are removed in vacuo, affording a light brown viscous oil. The [1]HMR spectrum confirms the following structure:

$Cl_3Sn—CH_2CH_2—CN.2$ DMF

Analysis: Sn found: 32.7%.

(b) Manufacture of the stabiliser 4.85 g (0.01 mole) of β-cyanoethyltin trichloride.2 DMF of Example 1 (a) are dissolved in 100 ml of chloroform and then 10.8 g (0.036 mole) of $HS—CH_2—COO(n-C_{14}H_{29})$ are added. With stirring, 3.4 g (0.04 mole) of $NaHCO_3$ are then added in portions. The reaction mixture is thereafter heated at reflux ($50°$ C.) for 2 to 3 hours, then cooled to about $20°$ C., and the water of reaction is removed as an azeotrope. NaCl is removed by filtration and volatile constituents are removed in vacuo. The product is a colourless liquid. The [1]HMR spectrum confirms the following structure:

$(n-C_{14}H_{29}—OOC—CH_2—S)_3Sn—CH_2Ch_2—CN$

Analysis: Sn found: 10.8%; $n_D^{20} = 1.5531$.

EXAMPLE 2

(a) Manufacture of the intermediate

The procedure of Example 1 (a) is repeated, using 116.4 g (0.39 mole) of bis-($\beta$-carbaminoethyl)tin dichloride in 400 ml of dimethyl formamide and 93 g (0.78 mole) of $SOCl_2$.

The $^1$HMR spectrum confirms the following structure:

$Cl_2Sn$–$(CH_2CH_2$–$CN)_2$.2 DMF

Analysis: Cl found: 26.8%.

(b) Manufacture of the stabiliser

The procedure of Example 1 (b) is repeated, using 15.1 g (0.06 mole) of bis-(cyanoethyl)tin dichloride.2 DMF, 36.2 g (0.12 mole) of tetradecyl thioglycolate and 10.8 g (0.13 mole) of sodium bicarbonate. The product is (n-$C_{14}H_{29}$—OOC—$CH_2$—S)$_2$Sn(—$CH_2CH_2$—CN)$_2$ Analysis: Sn found: 15.2%; $n_D^{20}$ = 1.4978.

EXAMPLE 3

Static heat test

A dry blend consisting of 100 parts of PVC (Solvic 264 GA; Deutsche Solvay-Werke), 0.2 part of lubricant (Wax E, Deutsche Solvay-Werke), and 1.5 parts of the stabiliser of Example 1 (b) is rolled for 5 minutes at 180° C. on mixer rolls, and afterwards a sample of sheet with a thickness of 0.12 mm is taken. The sample is subjected to heat in an oven at 180° C. for 45 minutes and the thermal ageing is determined according to the Yellowness Index (Y.I) of ASTM-D 1925-70. Y.I.=26.0.

EXAMPLE 4

The test is carried out by the same method as described in Example 3, except that the dry blend contains 1.4 parts of the stabiliser of Example 2 (b). After a thermal ageing of 45 minutes, the Yellowness Index is 50.8.

What is claimed is:

1. A compound of the formula I

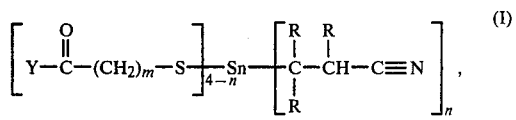

wherein each R independently is hydrogen or $C_1$–$C_4$ alkyl, Y is the —OR' or —S—R" group, in which R' is $C_{12}$–$C_{16}$ alkyl and R" is $C_8$–$C_{20}$ alkyl, $C_2$–$C_{20}$ alkenyl, $C_6$–$C_{20}$ aryl or $C_7$–$C_{20}$ aralkyl, m is an integer from 1 to 6, and n is 1 or 2.

2. A compound of the formula I according to claim 1, wherein Y is the —OR' group, in which R' is $C_{12}$–$C_{16}$ alkyl and m is 1 or 2.

3. A compound of the formula I according to claim 1, wherein n is 1.

4. A compound of the formula I according to claim 1, wherein each R independently is hydrogen or methyl.

5. Cyanoethyltin tris(tetradecyl thioglycolate) of the formula I according to claim 1.

6. A compound according to claim 1 of the formula (n-$H_{29}C_{14}$O.CO($CH_2$)$_p$S)$_3$≡Sn—$CH_2CH_2$—CN, wherein p is 1 or 2.

7. A compound according to claim 1 of the formula (n-$H_{29}H_{14}$O.CO$CH_2$S)$_3$≡Sn—$CH_2CH_2$—CN.

8. A stabilised halogen-containing thermoplastic which contains an effective stabilizing amount of a compound of the formula I according to claim 1.

9. A stabilised halogen-containing thermoplastic according to claim 8 which is polyvinyl chloride.

10. A method for stabilizing halogen-containing thermoplastic polymers against the degradative effects of heat and light which comprises incorporating into said thermoplastic an effective stabilizing amount of a compound according to claim 1.

* * * * *